United States Patent
Park et al.

(10) Patent No.: US 10,479,621 B2
(45) Date of Patent: Nov. 19, 2019

(54) CONTAINER SEARCH SYSTEM

(71) Applicant: KOREA INSTITUTE OF OCEAN SCIENCE & TECHNOLOGY, Ansan-si (KR)

(72) Inventors: Jong Won Park, Daejeon (KR); So Young Sung, Seoul (KR); Jung Hee Lee, Daejeon (KR); Yong Kon Lim, Daejeon (KR)

(73) Assignee: KOREA INSTITUTE OF OCEAN SCIENCE & TECHNOLOGY, Ansan-si (KR)

( * ) Notice: Subject to any disclaimer, the term of this patent is extended or adjusted under 35 U.S.C. 154(b) by 0 days.

(21) Appl. No.: 15/576,754

(22) PCT Filed: Feb. 28, 2017

(86) PCT No.: PCT/KR2017/002179
§ 371 (c)(1),
(2) Date: Nov. 24, 2017

(87) PCT Pub. No.: WO2017/164529
PCT Pub. Date: Sep. 28, 2017

(65) Prior Publication Data
US 2019/0009996 A1 Jan. 10, 2019

(30) Foreign Application Priority Data
Mar. 24, 2016 (KR) .......................... 10-2016-0035056

(51) Int. Cl.
*B65G 63/00* (2006.01)
*B61B 13/00* (2006.01)
(Continued)

(52) U.S. Cl.
CPC ............ *B65G 63/004* (2013.01); *B60L 15/20* (2013.01); *B60L 50/50* (2019.02); *B61B 13/00* (2013.01);
(Continued)

(58) Field of Classification Search
None
See application file for complete search history.

(56) References Cited

U.S. PATENT DOCUMENTS

2008/0025825 A1* 1/2008 Fujiwara .............. B65G 63/004
414/279

FOREIGN PATENT DOCUMENTS

JP 07-231515 8/1995
JP 3970315 9/2007
(Continued)

*Primary Examiner* — Hoon K Song
(74) *Attorney, Agent, or Firm* — Lex IP Meister, PLLC

(57) ABSTRACT

The present invention relates to a container search system comprising: a radiation irradiation unit for irradiating radiation to a container to be inspected; a detection unit installed opposite to the radiation irradiation unit to detect radiation having passed through a container; a transfer cart for loading an automobile thereon, on which a container to be inspected is loaded, and travelling along a search path formed between the radiation irradiation unit and the detection unit; and a circulation orbit unit formed to allow the transfer cart to circulate along the search path, wherein a primary side of a linear induction motor for generating a moving magnetic field is formed on either side among the transfer cart and the search path and a secondary-side reaction plate for inducing a secondary eddy current due to the moving magnetic field and generating a linear driving force is formed on the other side thereof. The container search system can transfer a
(Continued)

transfer cart according to a linear motor scheme in a radiation search section, and thus can obtain a radiation search image of high quality.

3 Claims, 6 Drawing Sheets

(51) Int. Cl.
    *B60L 15/20*     (2006.01)
    *B65G 49/00*     (2006.01)
    *G01N 23/04*     (2018.01)
    *G05D 1/02*     (2006.01)
    *B60L 50/50*     (2019.01)
    *G01V 5/00*     (2006.01)

(52) U.S. Cl.
    CPC ............. *B65G 49/00* (2013.01); *G01N 23/04* (2013.01); *G01V 5/0066* (2013.01); *G05D 1/02* (2013.01); *B65G 2201/0294* (2013.01); *G01V 5/0008* (2013.01); *Y02T 10/7005* (2013.01); *Y02T 10/7275* (2013.01)

(56) References Cited

FOREIGN PATENT DOCUMENTS

| | | |
|---|---|---|
| JP | 2014-511492 | 5/2014 |
| KR | 20-0403672 | 12/2005 |
| KR | 10-1352009 | 1/2014 |

\* cited by examiner

CONTAINER SEARCH SYSTEM

TECHNICAL FIELD

The present invention relates to a container search system, and more particularly, to a container search system capable of performing a search by irradiating radiation toward a vehicle, on which a container is loaded, while transferring the vehicle via a transfer cart in an unmanned state.

BACKGROUND ART

Generally, a container is widely used to carry cargo.

Such a container is conveyed to a destination through a transport device, such as a vehicle and a vessel.

Meanwhile, when imported or exposed cargo is transported overseas through a harbor, an inspection needs to be performed on cargo loaded on a container to check for the existence of smuggled goods or dangerous articles.

Recently, instead of using a method in which containers to be inspected are opened one by one and inspected by an inspector, a method of inspecting cargo by seeing an inside of a container using an X-ray detector has been introduced.

Since the recent container inspection method uses X-rays having a strong penetrating power, unmanned workplaces are required such that a driver or a worker is not affected by radiation emitted in the inspection process. Registered Utility model No. 20-0403672 discloses a container car transferring device for automation of a workplace.

However, since the transferring device is designed with a roller rotated by power of a motor and traveling on a rail, vibration due to contact between the roller and the rail may be applied to the entire transferring device during travelling and cause quality of a search image of X-rays to be degraded.

Accordingly, there is a need for a container transferring structure capable of stably maintaining quality of a search image.

DISCLOSURE

Technical Problem

The present invention is directed to providing a container search system capable of obtaining a high quality radiation image of a container while transferring a container loaded vehicle in an unmanned state with minimum vibration.

Technical Solution

One aspect of the present invention provides a container search system including: a radiation irradiator configured to emit radiation toward a container to be inspected; a detector installed opposite the radiation irradiator to detect radiation passed through the container; a transfer cart configured to load a vehicle, which carries the container, and travel along a search path formed between the radiation irradiator and the detector; and a circulation orbit allowing the transfer cart to circulate along the search path, wherein a primary side of a linear induction motor configured to generate a moving magnetic field is formed on one of the transfer cart and the search path, and a secondary-side reaction plate configured to generate a linear driving force by inducing a secondary eddy current due to the moving magnetic field is formed on the other one of the transfer cart and the search path.

The transfer cart may include: a LIM part provided in a middle of the transfer cart to extend in a longitudinal direction thereof and having the primary side of the linear induction motor; vehicle wheel seating parts extending from both sides of the LIM part in a transverse direction crossing the longitudinal direction of the LIM part, and the vehicle wheel seating parts are configured to provide an entry region in which wheels of the vehicle carrying the container enter, and having seating grooves in which the wheels of the vehicle are seated; and side parts extending from the vehicle wheel seating parts in the transverse direction.

The side part may be provided with a current collecting terminal configured to receive power required for operating the LIM part while maintaining contact with a power supply rail which is installed to be parallel with the search path and supply the power thereto.

The side part may include: a plurality of running wheels configured to be run when the LIM part is in a non-driven state; a running wheel driving part configured to drive the running wheels; and a control part configured to control driving of the running wheel driving part.

The side part may further include: a plurality of lifting wheels installed to perform a rolling movement in a direction perpendicular to the longitudinal direction of the LIM part to be used when the transfer cart departs from the circulation orbit; and a lifting unit allowing the side part to ascend or descend with respect to the lifting wheels.

The control part may perform control such that the LIM part is operated in the search path on which the secondary-side reaction plate is formed, and control the running wheel driving part such that the running wheels runs in a return path remaining outside the search path.

Advantageous Effects

As should be apparent from the above, a container search system according to the present invention can transfer a transfer cart in a radiation search section using a linear motor scheme to obtain a high quality radiation search image.

MODES OF THE INVENTION

Hereinafter, a container search system according to an exemplary embodiment of the present invention will be described in detail with reference to the accompanying drawings.

Figure 1:
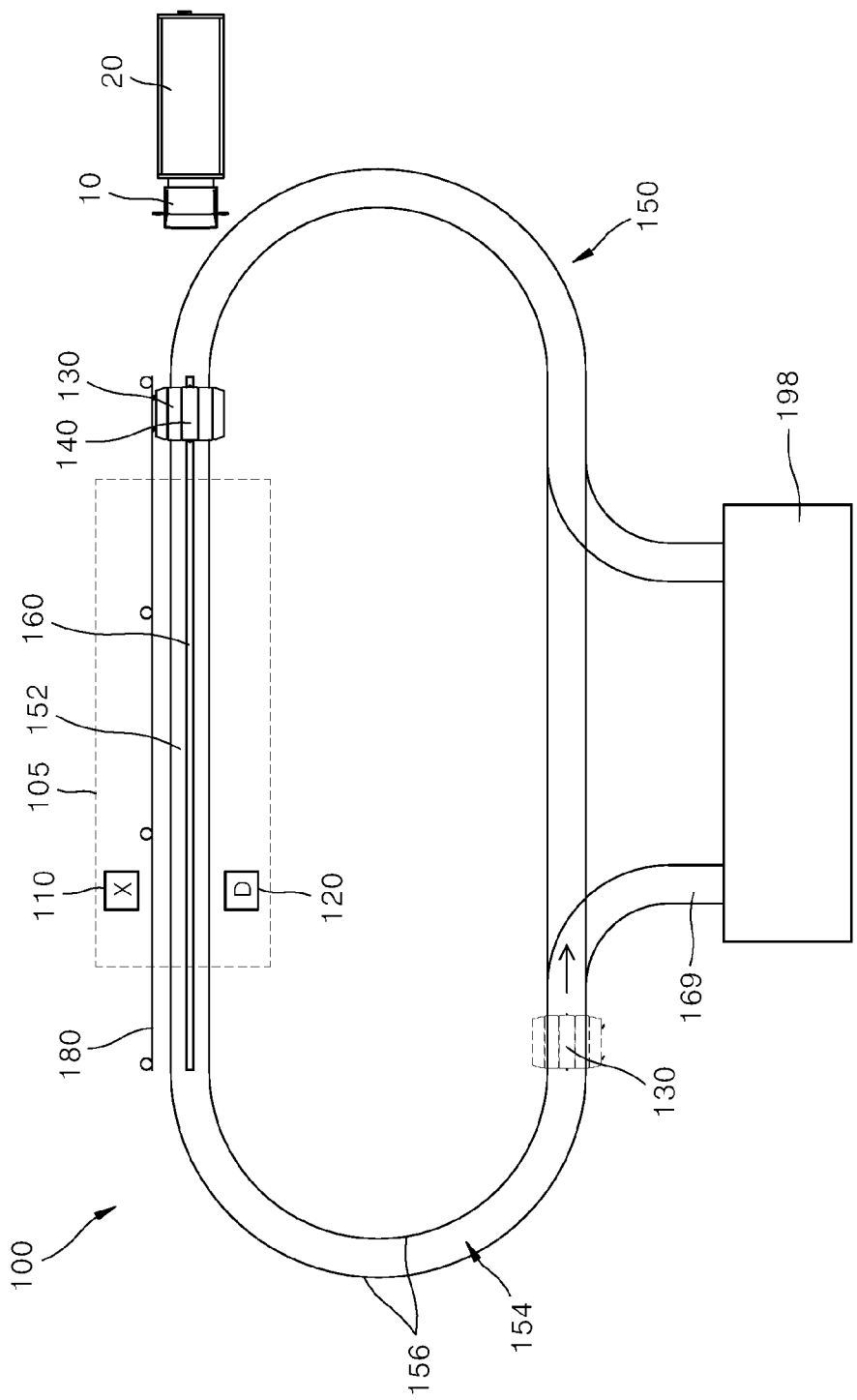
FIG. 1 is a view illustrating a container search system according to the present invention.
Figure 2:
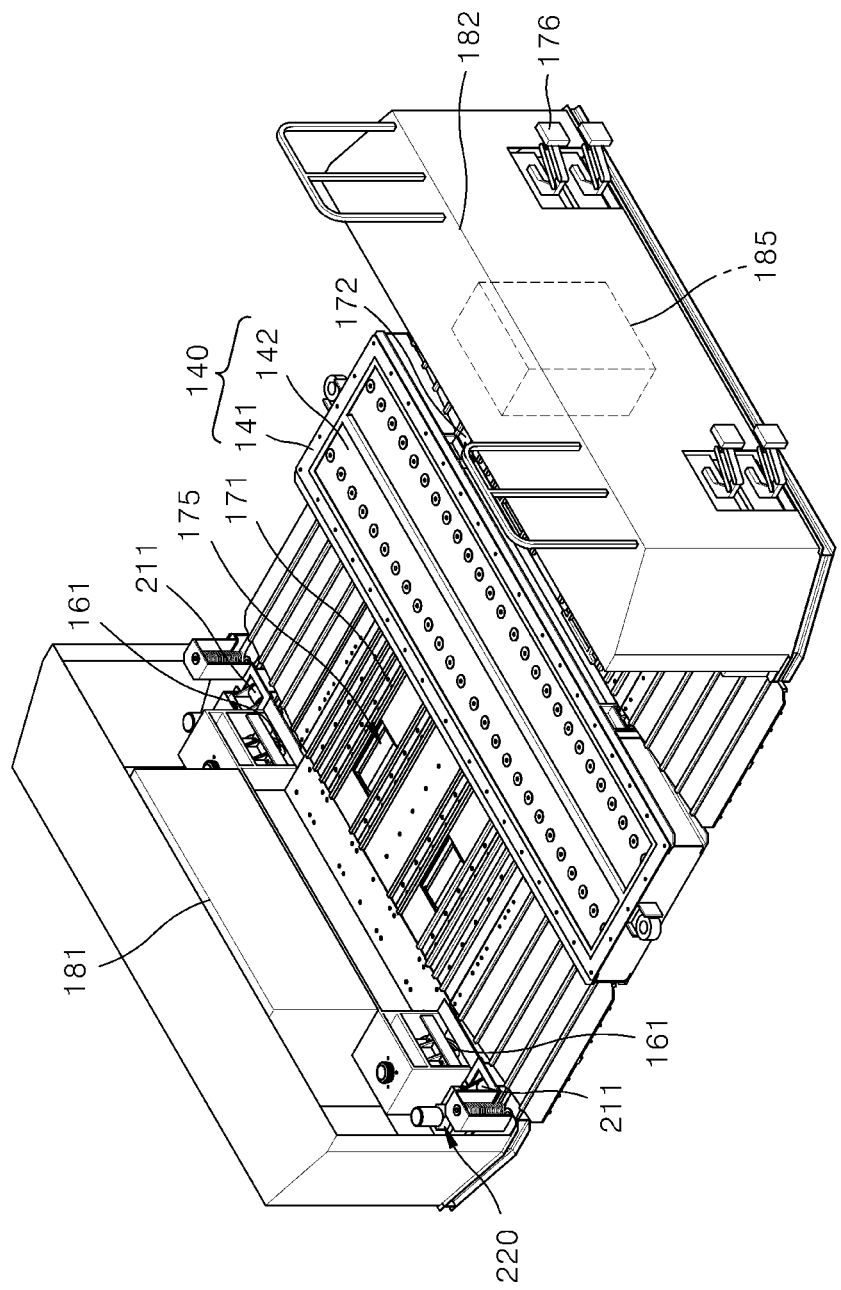
FIG. 2 is a perspective view illustrating a transfer cart shown in FIG. 1.
Figure 3:
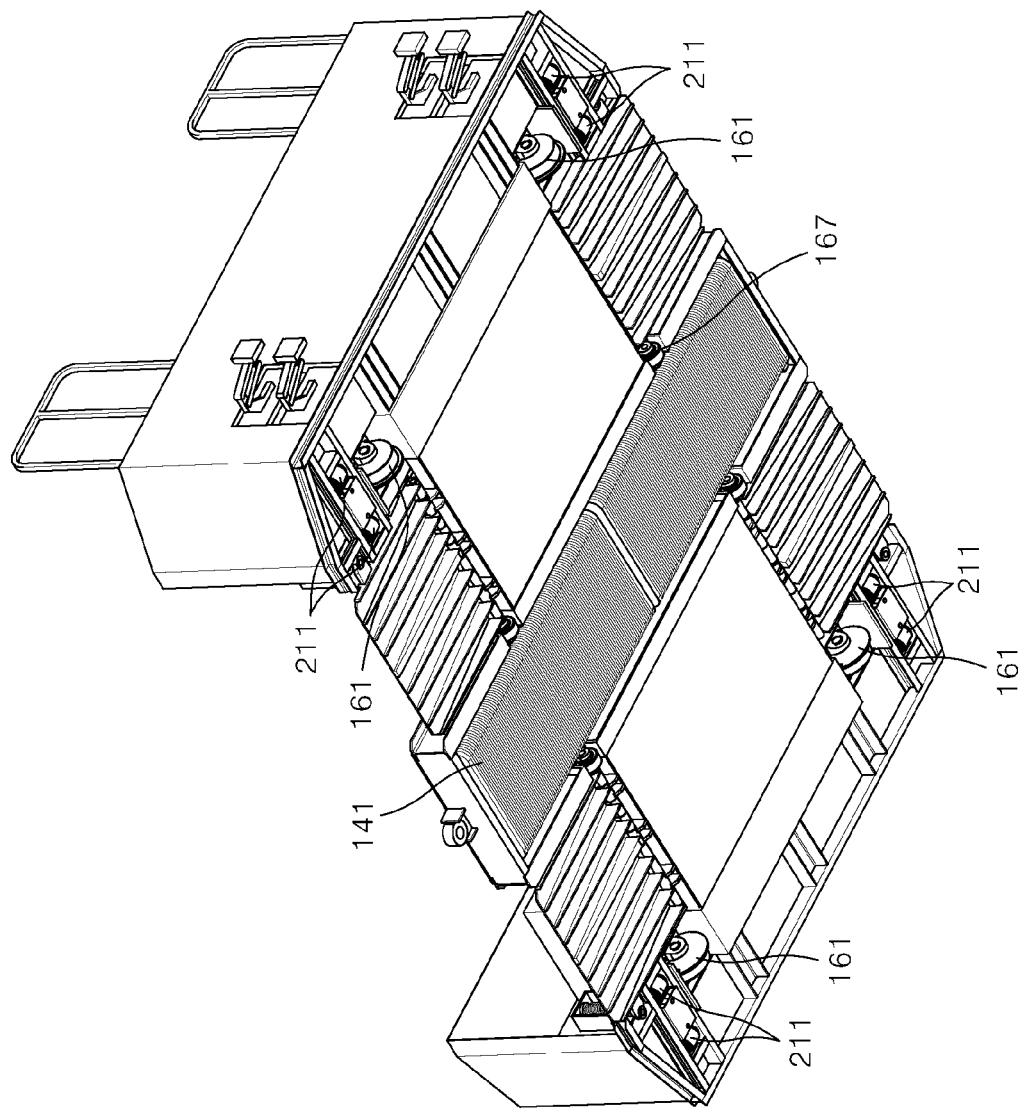
FIG. 3 is a perspective view illustrating viewed at an angle in which a bottom surface of the transfer cart of FIG. 2 is exposed.
Figure 4:
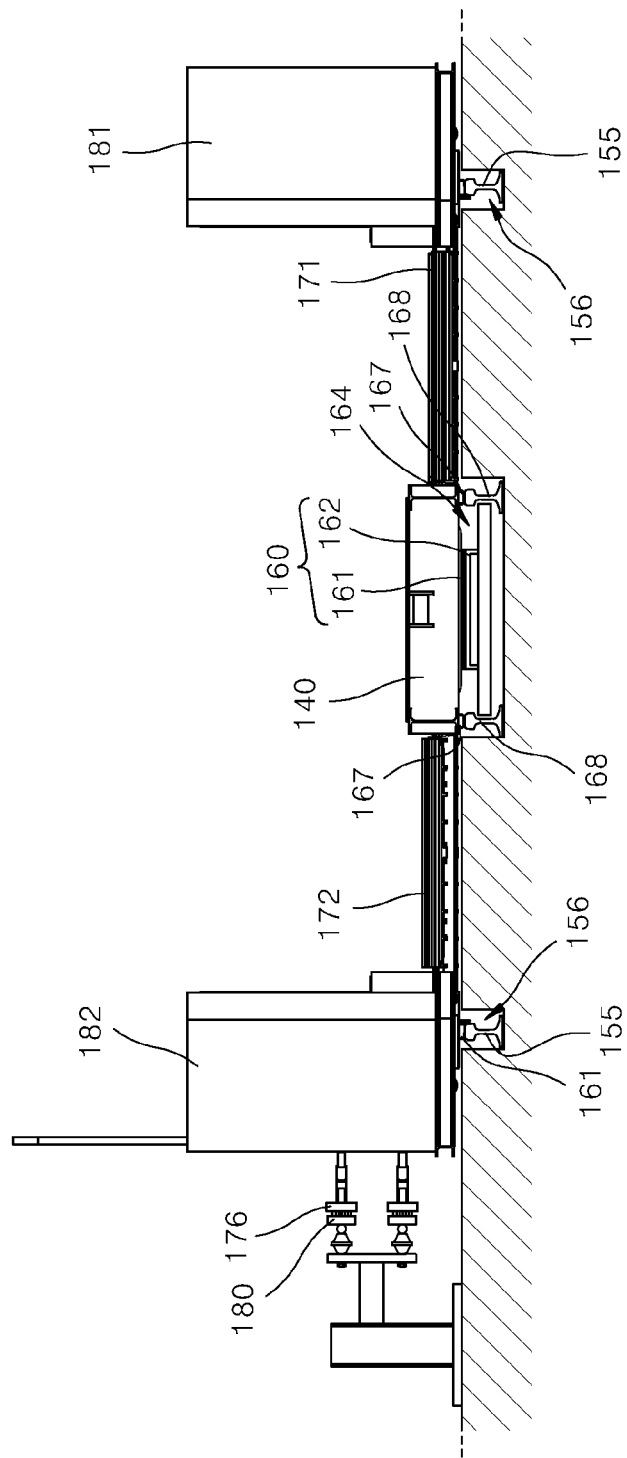
FIG. 4 is a view illustrating a state in which the transfer cart is disposed on a travelling path.

FIG. 1 is a view illustrating a container search system according to the present invention.

Referring to FIG. 1, a container search system 100 according to the present invention includes a radiation irradiator (X) 110, a detector (D) 120, a transfer cart 130, and a circulation orbit 150.

The radiation irradiator 110 is installed to emit radiation, such as X-rays, toward a container 20 to be inspected and transferred along a search path 152.

The search path 152 refers to a linearly extended section having a predetermined length such that a search image corresponding to the radiation irradiation is acquired while the container 20 is being transferred via the transfer cart 130, and in the illustrated example, the search path 152 corresponds to a section provided with a secondary-side reaction plate 160, which will be described below.

The detector 120 is installed at a side opposite the radiation irradiator 110 with respect to the search path 152 to face the radiation irradiator 110.

The detector 120 detects radiation passed through the container 20, acquires scanning information of the container 20, i.e., a search image, from the detected radiation, and processes the scanning information in a predetermined processing scheme.

The radiation irradiator 110 and the detector 120 are paired with each other to form a unit inspection part for acquiring inspection information about the inside of the scanned container 20.

A shielding wall 105 is provided at a portion of the search path 152 to form an internal space which is closed to prevent radiation from being exposed to the outside, and doors may be provided at an entrance and an exit of the shielding wall 105 to open and close the internal space.

The transfer cart 130 is configured to load a vehicle 10, which carries the container 20, and travel along the search path 152 formed between the radiation irradiator 110 and the detector 120 in an unmanned state.

The transfer cart 130 is configured to be levitated and propelled by a moving magnetic field being generated between the search path 152 and the transfer cart 130.

In this case, a primary side of a linear induction motor is provided on one of the transfer cart 130 and the search path 152 to generate the moving magnetic field, and a secondary-side reaction plate is provided on the other of the transfer cart 130 and the search path 152 to generate a linear driving force by inducing a secondary eddy current due to the moving magnetic field.

In this embodiment, the transfer cart 130 is provided with a LIM part 140, which corresponds to the primary side of the linear induction motor, and the search path 152 is provided with a secondary-side reaction plate 160 to generate a linear driving force by inducing a secondary eddy current due to a moving magnetic field of the LIM part 140.

Hereinafter, a detailed structure of the transfer cart 130 will be described with reference to FIGS. 2 to 7.

The transfer cart 130 includes the LIM part 140, first and second vehicle wheel seating parts 171 and 172, and first and second side parts 181 and 182.

The LIM part 140, the first and second vehicle wheel seating parts 171 and 172, and the first and second side parts 181 and 182 are connected to be levitated as one unit.

The LIM part 140 includes an accommodation frame 141 provided at a middle thereof in a rectangular shape extending along a longitudinal direction of the LIM part 140, and a moving magnetic field generating unit 142 formed inside the accommodation frame 141 and having the primary side element of the linear motor generating the moving magnetic field.

The moving magnetic field generating unit 142 corresponding to the primary side element of the liner motor may employ a general structure in which an induction motor along is cut in an axial direction and a stator side thereof is expanded in a planar state.

The secondary-side reaction plate 160 installed in the middle of the search path 152 and extending in the form of a straight line may employ a structure including an upper plate 161 formed of copper or aluminum and a lower plate 162 provided below the upper plate 161 and formed of iron.

The first and second vehicle wheel seating parts 171 and 172 extend from both longitudinal-direction-parallel sides of the accommodation frame 141 of the LIM part 140 in a transverse direction crossing the longitudinal direction of the LIM part 140, provide an entry region into which wheels of the vehicle 10 carrying the container 20 enter, and have seating grooves 175 in which the wheels of the vehicle 10 are seated.

The first and second side parts 181 and 182 extend from the first and second vehicle wheel seating parts 171 and 172 in the transverse direction crossing the longitudinal direction of the LIM part 140.

One of the first and second side parts 181 and 182 located at the outer most side with respect to a travelling direction of the transfer cart 130 is provided with a current collecting terminal 176 which is installed to be exposed to the outside to receive power required for operating the LIM part 140 while maintaining contact with a power supply rail 180 installed to be parallel with the search path 152 and supply the power thereto.

In this embodiment, the second side part 182 is provided with the current collecting terminal 176.

The second side part 182 is provided with an energy storage device 185 to store power supplied through the current collecting terminal 176 and use the power.

The energy storage device 185 is configured to be charged by the power supplied through the current collecting terminal 176 and allow the charged power to be used when driving an operating component including a running wheel driving part 165, which will be described below.

Meanwhile, the first and second side parts 181 and 182 are provided with four running wheels 161 allowing the transfer cart 130 to travel when the LIM part 140 is in a non-driven state.

The running wheels 161 are provided to be rotated and driven by power supplied thereto by the running wheel driving part 165.

The running wheel driving part 165 is controlled by a control part 191 to drive a motor, which is provided to drive the running wheels 161 with the power supplied from the energy storage device 185.

When the LIM part 140 is operated so that the transfer cart 130 is levitated to be spaced apart from the secondary-side reaction plate 160 and is propelled by the moving magnetic field, the running wheels 161 are spaced apart from a running rail 155, and when the LIM part 140 is not operated so that the transfer cart 130 descends to the secondary-side reaction plate 160, the running wheels 161 enter an initial state while in close contact with the running rail 155.

In addition, the first and second side parts 181 and 182 include a plurality of lifting wheels 211 that are installed to perform a rolling movement in a direction perpendicular to the longitudinal direction of the LIM part 140 to be used when the transfer cart 130 departs from the search path 152 or a return path 154 of the circulation orbit 150, and a lifting unit 220 allowing the first and second side parts 181 and 182 to ascend or descend with respect to the lifting wheels 211.

Figure 5:
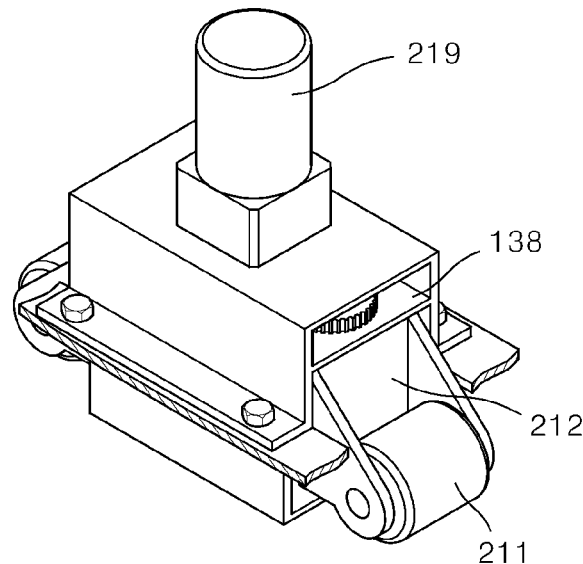
FIG. 5 is a view illustrating a portion of a lifting wheel installed on the transfer cart shown in FIG. 2.
Figure 6:
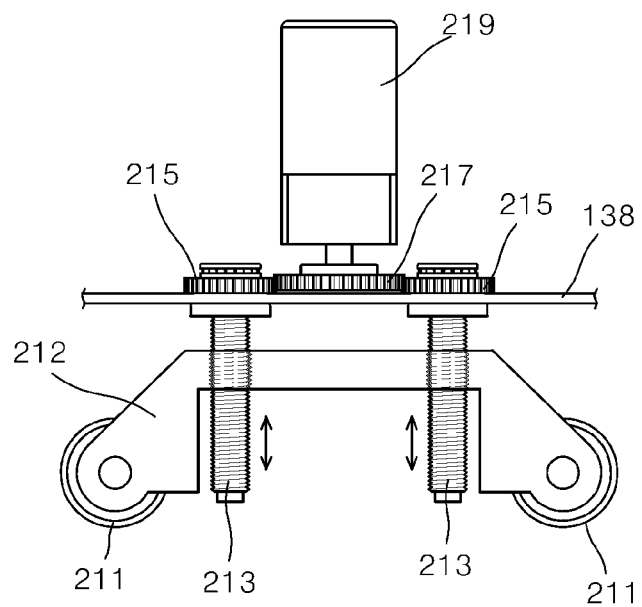
FIG. 6 is a view separately illustrating a lifting unit cover shown in FIG. 5.
Figure 7:
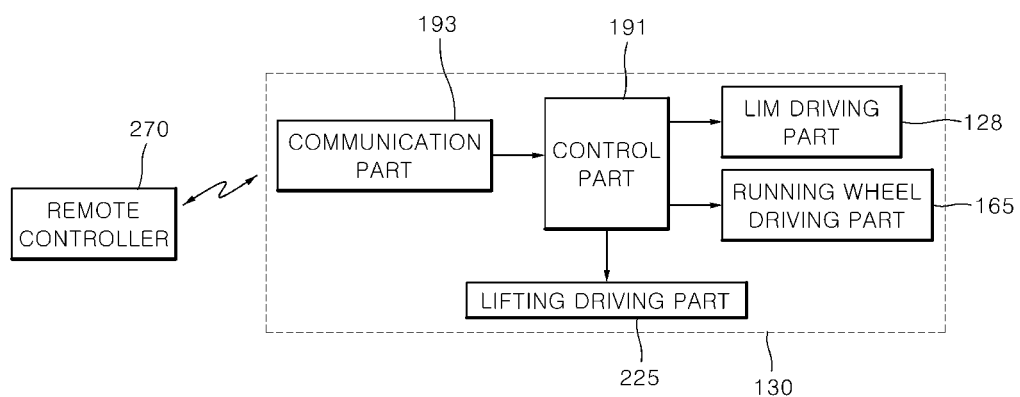
FIG. 7 is a block diagram illustrating elements for controlling the transfer cart shown in FIG. 1.

Referring to FIGS. 5 and 6, the lifting unit 220 includes two lifting screws 213 vertically coupled to a support bracket 212 rotatably supporting two adjacent lifting wheels 211 to ascend and descend by rotation, a lifting motor 219 allowing the lifting screws 213 to ascend and descend by rotating a driving gear 217 engaged with a driven gear 215 formed in the lifting screw 213, and a lifting driving part 225 configured to drive the lifting motor 219.

When the driving gear 217 rotates in a first direction, the two lifting screws 213 ascend together, and when the driving gear 217 rotates in a second direction opposite the first direction, the two lifting screws 213 descend together.

Although the lifting driving part 225 is illustrated as being controlled to be driven by the control part 191, which will be described below, it should be understood that the lifting driving part 225 may be provided to be driven by an additional manipulation switch unlike the illustrated example.

The lifting screw 213 is installed to be rotated in place on a main frame 138 separated from the support bracket 212 and disposed opposite an upper portion thereof.

The main frame 138 is a portion extending from the LIM part 140 and integrated with the first and second vehicle wheel seating parts 171 and 172.

The lifting unit 220 may be used to raise the transfer cart 130 up to a height at which the running wheels 161 escape from rail grooves 156, which will be described below, when it is necessary to separate the transfer cart 130 from the rail grooves 156 due to a malfunction or any other reason.

Meanwhile, the control part 191 mounted on the transfer cart 130 controls driving of the LIM part 140 and the running wheel driving part 128 driving the running wheels 161 of the transfer cart 130 according to a running manipulation signal received through a communication part 193 in a wireless scheme from a remote controller 270 for remotely controlling driving of the transfer cart 130.

Preferably, the control part 191 controls the LIM driving part 128 to operate the LIM part 140 while the transfer cart 130 travels on the search path 152 of the circulation orbit 150, and controls the running wheel driving part 165 such that the running wheels 161 perform travelling on the return path 154 remaining outside the search path 152.

The circulation orbit 150 takes the form of a circulation orbit such that the transfer cart 130 circulates along the search path 152.

The circulation orbit 150 may be divided into the search path 152 extending in the form of a straight line and having the secondary-side reaction plate 160 formed thereon to propel the transfer cart 130 due to the moving magnetic field, and the return path 154 extending from a trailing end of the search path 152 to a leading end of the search path 152.

Meanwhile, both of the search path 152 and the return path 154 are provided with the running wheel rail groove 156 recessed downward in the form of a circular track such that the running wheels 161 may travel therein, and the running wheel rail groove 156 has the running rail 155 installed therein to be separated from or come into contact with the running wheels 161 depending on whether the transfer cart 130 is in an upwardly levitated state or in a non-levitated state.

In addition, only the search path 152 is provided with a central portion groove 164 recessed downward and having the secondary-side reaction plate 160 formed therein.

The return path 154 is provided with a junction path 169 for transferring the transfer cart 130 to a repair warehouse 198 in which the transfer cart 130 may be repaired when necessary.

In addition, the central portion groove 164 is provided with an auxiliary rail 168 enabling an auxiliary roller 167 formed on the transfer cart 130 to perform a rolling movement in a contact state at a time of non-levitation.

Accordingly, when a driver gets off the vehicle 10 after the wheels of the vehicle 10 are seated on the first and second vehicle wheel seating parts 171 and 172 of the transfer cart 130 waiting at a front end of the search path 152, the control part 191 controls the LIM driving part 128 to operate the LIM part 140 according to a travelling control signal instructed through the remote controller 270 such that the transfer cart 130 is levitated and travels on the search path 152 at a constant velocity, and in this process, a scanned search image of the container 20 is obtained.

Then, when the transfer cart 130 passing by the shielding wall 105 reaches the trailing end of the search path 152, the transfer cart 130 is controlled to stop until the driver gets back on the vehicle 10, and when the vehicle 10 is then separated from the transfer cart 130, the transfer cart 130 is controlled to move to the leading end of the search path 152 by the running wheels 161 being driven along the return path 154 again.

According to the container search system 100, the transfer cart 130 can be transferred to the search path 152 with almost no vibration through a linear motor scheme so that a high quality radiation search image can be acquired.

The invention claimed is:

1. A container search system comprising:
    a radiation irradiator configured to emit radiation toward a container to be inspected;
    a detector installed opposite the radiation irradiator to detect radiation passed through the container;
    a transfer cart configured to load a vehicle, which carries the container, and travel along a search path formed between the radiation irradiator and the detector; and
    a circulation orbit allowing the transfer cart to circulate along the search path,
    wherein a primary side of a linear induction motor configured to generate a moving magnetic field is formed on one of the transfer cart and the search path, and a secondary-side reaction plate configured to generate a linear driving force by inducing a secondary eddy current due to the moving magnetic field is formed on the other one of the transfer cart and the search path,
    wherein the transfer cart includes:
    a LIM part provided in a middle of the transfer cart to extend in a longitudinal direction of the transfer cart, and having the primary side of the linear induction motor formed therein;
    vehicle wheel seating parts formed to extend from both sides of the LIM part in a transverse direction crossing the longitudinal direction of the LIM part, and the vehicle wheel seating parts are configured to provide an entry region into which wheels of the vehicle carrying the container enter, and having seating grooves in which the wheels of the vehicle are seated; and
    side parts extending from the vehicle wheel seating parts in the transverse direction, and
    wherein the side part includes:
    a plurality of running wheels configured to be run when the LIM part is in a non-driven state;
    a running wheel driving part configured to drive the running wheels; and
    a control part configured to control driving of the running wheel driving part.

2. The container search system of claim 1, wherein the side part further includes:
    a plurality of lifting wheels installed to perform a rolling movement in a direction perpendicular to the longitudinal direction of the LIM part to be used when the transfer cart from departs the circulation orbit; and a lifting unit allowing the side part to ascend or descend with respect to the lifting wheels.

3. The container search system of claim 1, wherein the control part performs control such that the LIM part is operated in the search path on which the secondary-side reaction plate is formed, and controls the running wheel driving part such that the running wheels runs in a return path remaining outside the search path.

* * * * *